(12) United States Patent
Ro et al.

(10) Patent No.: US 7,961,841 B2
(45) Date of Patent: Jun. 14, 2011

(54) X-RAY PHOTOGRAPHING APPARATUS

(75) Inventors: Chang Joon Ro, Seongnam-si (KR); Tae Woo Kim, Hwaseong-si (KR)

(73) Assignees: Vatech Co., Ltd., Hwaseong-Si, Gyeonggi-Do (KR); Vatech Ewoo Holdings Co., Ltd., Yongin-Si, Kyunggi-Do (KR)

( * ) Notice: Subject to any disclaimer, the term of this patent is extended or adjusted under 35 U.S.C. 154(b) by 0 days.

(21) Appl. No.: 12/311,698

(22) PCT Filed: Oct. 10, 2007

(86) PCT No.: PCT/KR2007/004927
§ 371 (c)(1), (2), (4) Date: May 27, 2009

(87) PCT Pub. No.: WO2008/044861
PCT Pub. Date: Apr. 17, 2008

(65) Prior Publication Data
US 2010/0195786 A1    Aug. 5, 2010

(30) Foreign Application Priority Data

Oct. 10, 2006   (KR) .................. 10-2006-0098480

(51) Int. Cl.
*A61B 6/14*    (2006.01)
*H05G 1/58*    (2006.01)

(52) U.S. Cl. ............. 378/38; 378/19; 378/116; 378/191

(58) Field of Classification Search .................. 378/19, 378/38, 116, 191
See application file for complete search history.

(56) References Cited

U.S. PATENT DOCUMENTS

| | | | |
|---|---|---|---|
| 5,692,027 A | 11/1997 | Yoshimura et al. | |
| 6,466,641 B1 * | 10/2002 | Virta et al. | 378/38 |
| 7,103,141 B2 * | 9/2006 | Sonobe et al. | 378/39 |
| 7,424,091 B2 * | 9/2008 | Park et al. | 378/39 |
| 7,577,232 B2 * | 8/2009 | Tachibana et al. | 378/39 |
| 7,720,191 B2 * | 5/2010 | Muller | 378/38 |
| 2006/0256921 A1 | 11/2006 | Tachibana et al. | |
| 2009/0168966 A1 * | 7/2009 | Suzuki et al. | 378/116 |
| 2010/0128840 A1 * | 5/2010 | Cha | 378/4 |

FOREIGN PATENT DOCUMENTS

| | | |
|---|---|---|
| CN | 1787780 A | 6/2006 |
| DE | 197 54 670 A1 | 10/1998 |
| EP | 0 632 994 A1 | 11/1995 |
| JP | 11-318886 A | 11/1999 |
| KR | 20-2002-0032766 B1 | 11/2002 |
| WO | 2007/018333 A1 | 2/2007 |

OTHER PUBLICATIONS

Examination Opinion for Application No. EP07833 238.4, three (3) pages.
Supplementary European Search Report for Application No. EP07833 238.4, two (2) pages.
PCT Written Opinion of the International Searching Authority for PCT/KR2007/004927, four (4) pages.
PCT International Search Report for PCT/KR2007/004927, three (3) pages.

* cited by examiner

*Primary Examiner* — Edward J Glick
*Assistant Examiner* — Thomas R Artman
(74) *Attorney, Agent, or Firm* — The Nath Law Group; Jerald L. Meyer; Sungyeop Chung (57) ABSTRACT

The present invention relates to an X-ray photographing apparatus that is capable of being automatically transformed to panoramic, CT, and cephalometric photographing apparatuses having corresponding modes in accordance with the mounting or demounting of a panoramic sensor, a CT sensor, or a cephalometric sensor thereon/therefrom, thereby at once performing the photographing for the images being the corresponding modes.

4 Claims, 10 Drawing Sheets

X-RAY PHOTOGRAPHING APPARATUS

This is an National Phase Application filed under 35 U.S.C. 371 as a national stage of PCT/KR2007/004927, with the filing date of 10 Oct., 2007, an application claiming the benefit of Korean Patent Application No. 10-2006-0098480, filed on 10 Oct. 2006, the entire content of which is hereby incorporated by reference in its entirety.

TECHNICAL FIELD

The present invention relates to an X-ray photographing apparatus, and more particularly, to an X-ray photographing apparatus that is capable of being automatically transformed to a panoramic, CT, or cephalometric photographing apparatus of a corresponding mode in accordance with the mounting or demounting of a panoramic sensor, a computerized tomography (CT) sensor, or a cephalometric sensor thereonto/therefrom.

BACKGROUND ART

In dental treatment field, a CT X-ray photographing apparatus is used to radiate a given amount of X-ray beams to a set of teeth to be photographed, to measure the amount of X-ray beam radiation by an X-ray sensor, to record the measured data on a memory, to obtain an X-ray absorbing rate of each point of the photographed region by a computer, and to reconstruct the obtained absorbing rate to an image. A panoramic X-ray photographing apparatus performs tomography while being rotated along a needed track in accordance with the shape of a dental arch, thereby performing tomography. A cephalometric X-ray photographing apparatus is mainly used to photograph a patient s head so as to perform orthodontic treatments or orthognathic surgery.

Using such the panoramic X-ray photographing apparatus, the CT X-ray photographing apparatus and the cephalometric X-ray photographing apparatus, a panoramic image, a CT image, and a cephalometric image can be obtained. If the images being photographed in a plurality of modes are to be obtained at once, however, they should be photographed individually by using the respective X-ray photographing apparatuses, which is actually cumbersome. In order to remove such the inconveniences in use, thus, there are proposed a variety of X-ray photographing apparatuses each providing the panoramic image, the CT image, and/or the cephalometric image in a single system. For example, a panoramic and CT X-ray photographing apparatus provides both of the panoramic image and the CT image, and a panoramic and cephalometric X-ray photographing apparatus provides both of the panoramic image and the cephalometric image. Like this, X-ray photographing apparatuses that provide images to be photographed in a plurality of modes at the same time have been proposed and developed.

However, the conventional X-ray photographing apparatuses should have a separate mode conversion means so as to obtain the images photographed in the plurality of modes at once, and also, the mode conversion has to be manually performed in accordance with the mode to be photographed, which makes it inconvenient to use.

DISCLOSURE OF INVENTION

Technical Problem

Accordingly, the present invention has been made to solve these problems, and it is an object of the present invention to provide an X-ray photographing apparatus that is capable of being automatically transformed to panoramic photographing, CT photographing, or cephalometric photographing apparatuses having a corresponding mode in accordance with the mounting or demounting of a panoramic sensor, a CT sensor, or a cephalometric sensor thereon/therefrom.

Technical Solution

To achieve the above object, according to an aspect of the present invention, there is provided an X-ray photographing apparatus having an X-ray light source unit for generating X-rays therefrom and an X-ray sensor unit for detecting the X-rays generated from the X-ray light source unit, wherein the X-ray sensor unit has at least one or more X-ray sensor mounting parts adapted to detachably mount one selected from the group consisting of a panoramic sensor, a CT sensor and a cephalometric sensor, such that if one sensor selected from the group consisting of the panoramic sensor, the CT sensor and the cephalometric sensor is mounted onto any one of the X-ray sensor mounting parts, the X-ray photographing apparatus is transformed to an X-ray photographing apparatus having a corresponding mode to the selected sensor.

To achieve the above object, according to another aspect of the present invention, there is provided an X-ray photographing apparatus having an X-ray light source unit for generating X-rays therefrom and an X-ray sensor unit for detecting the X-rays generated from the X-ray light source unit, wherein the X-ray sensor unit has a first sensor mounting part adapted to detachably mount a panoramic sensor thereonto and a CT sensor, such that if the panoramic sensor is mounted onto the first sensor mounting part, the X-ray photographing apparatus is transformed to a panoramic X-ray photographing apparatus, and if the panoramic sensor is demounted from the first sensor mounting part, the X-ray photographing apparatus is transformed to a CT X-ray photographing apparatus.

To achieve the above object, according to still another aspect of the present invention, there is provided an X-ray photographing apparatus having an X-ray light source unit for generating X-rays therefrom and an X-ray sensor unit for detecting the X-rays generated from the X-ray light source unit, wherein the X-ray sensor unit has a first sensor mounting part adapted to detachably mount a panoramic sensor thereonto and a CT sensor mounting part adapted to detachably mount a CT sensor thereonto, such that if the panoramic sensor is mounted onto the first sensor mounting part, the X-ray photographing apparatus is transformed to a panoramic X-ray photographing apparatus, and if the panoramic sensor is demounted from the first sensor mounting part and the CT sensor is mounted onto the CT sensor mounting part, the X-ray photographing apparatus is transformed to a CT X-ray photographing apparatus.

To achieve the above object, according to yet another aspect of the present invention, there is provided an X-ray photographing apparatus having an X-ray light source unit for generating X-rays therefrom and an X-ray sensor unit for detecting the X-rays generated from the X-ray light source unit, wherein the X-ray sensor unit has a CT sensor and a first sensor mounting part and a second sensor mounting part adapted to detachably mount an X-ray sensor used for panoramic photographing or cephalometric photographing thereonto, such that if the X-ray sensor is mounted onto the first sensor mounting part, the X-ray photographing apparatus is transformed to a panoramic X-ray photographing apparatus; if the X-ray sensor is mounted onto the second sensor mounting part, the X-ray photographing apparatus is transformed to a cephalometric X-ray photographing apparatus;

and if the X-ray sensor is demounted from the first sensor mounting part and the second sensor mounting part, the X-ray photographing apparatus is transformed to a CT X-ray photographing apparatus.

To achieve the above object, according to still yet another aspect of the present invention, there is provided an X-ray photographing apparatus having an X-ray light source unit for generating X-rays therefrom and an X-ray sensor unit for detecting the X-rays generated from the X-ray light source unit, wherein the X-ray sensor unit has a CT sensor mounting part adapted to detachably mount a CT sensor thereonto and a first sensor mounting part and a second sensor mounting part each adapted to detachably mount an X-ray sensor used for panoramic photographing or cephalometric photographing thereonto, such that if the X-ray sensor is mounted onto the first sensor mounting part, the X-ray photographing apparatus is transformed to a panoramic X-ray photographing apparatus; if the X-ray sensor is mounted onto the second sensor mounting part, the X-ray photographing apparatus is transformed to a cephalometric X-ray photographing apparatus; and if the X-ray sensor is demounted from the first sensor mounting part and the second sensor mounting part and the CT sensor is mounted onto the CT sensor mounting part, the X-ray photographing apparatus is transformed to a CT X-ray photographing apparatus.

To achieve the above object, according to another aspect of the present invention, there is provided an X-ray photographing apparatus having an X-ray light source unit for generating X-rays therefrom and an X-ray sensor unit for detecting the X-rays generated from the X-ray light source unit, wherein the X-ray sensor unit has a first sensor mounting part adapted to detachably mount a panoramic sensor thereonto and a CT sensor, such that if the panoramic sensor is mounted onto the first sensor mounting part, the X-ray photographing apparatus is transformed to a panoramic X-ray photographing apparatus, and if the first sensor mounting part is slid toward a predetermined direction, the X-ray photographing apparatus is transformed to a CT X-ray photographing apparatus.

To achieve the above object, according to another aspect of the present invention, there is provided an X-ray photographing apparatus having an X-ray light source unit for generating X-rays therefrom and an X-ray sensor unit for detecting the X-rays generated from the X-ray light source unit, wherein the X-ray sensor unit has a panoramic sensor, a CT sensor and a driving means, the driving means being adapted to rotatably drive the X-ray sensor unit with respect to a predetermined point between the panoramic sensor and the CT sensor, such that if the X-ray sensor unit is rotatably driven to face the panoramic sensor and the X-ray light source unit each other, the X-ray photographing apparatus is transformed to a panoramic X-ray photographing apparatus, and if the X-ray sensor unit is rotatably driven to face the CT sensor and the X-ray light source unit each other, the X-ray photographing apparatus is transformed to a CT X-ray photographing apparatus.

To achieve the above object, according to still yet another aspect of the present invention, there is provided an X-ray photographing apparatus having an X-ray light source unit for generating X-rays therefrom and an X-ray sensor unit for detecting the X-rays generated from the X-ray light source unit, wherein the X-ray sensor unit has a CT sensor and a first sensor mounting part and a second sensor mounting part each adapted to detachably mount an X-ray sensor used for panoramic photographing or cephalometric photographing thereonto, such that if the X-ray sensor is mounted onto the first sensor mounting part, the X-ray photographing apparatus is transformed to a panoramic X-ray photographing apparatus; if the X-ray sensor is mounted onto the second sensor mounting part, the X-ray photographing apparatus is transformed to a cephalometric X-ray photographing apparatus; and if the first sensor mounting part having the X-ray sensor mounted thereonto is slid toward a predetermined direction or if the X-ray sensor is demounted from the second sensor mounting part, the X-ray photographing apparatus is transformed to a CT X-ray photographing apparatus.

According to the features of the present invention, preferably the first sensor mounting part is located closer to the X-ray light source unit than the CT sensor is.

According to the features of the present invention, preferably, the X-ray light source unit has a driving means such that it is driven toward a direction adjacent to the X-ray sensor unit or distant therefrom.

ADVANTAGEOUS EFFECTS

According to the present invention, there is provided an X-ray photographing apparatus that is capable of being automatically transformed easily to a panoramic photographing apparatus, a CT photographing apparatus, or a cephalometric photographing apparatus having a corresponding mode in accordance with the mounting or demounting of a panoramic sensor, a CT sensor, or a cephalometric sensor thereonto/therefrom.

While the present invention will be described with reference to the particular illustrative embodiments, it is not to be restricted by the embodiments but only by the appended claims. It is to be appreciated that those skilled in the art can change or modify the embodiments without departing from the scope and spirit of the present invention.

EXPLANATION ON THE REFERENCE NUMERALS OF THE MAIN PARTS IN THE DRAWINGS

100, 200, 300, 400: X-ray photographing apparatus
110, 310: rotary arm
120, 320: X-ray light source unit
130, 230, 330, 430: X-ray sensor unit
140, 340: rotary arm-supporting member
131, 231, 331, 431: panoramic sensor
132, 232, 332, 432: first sensor mounting part
133, 233, 333, 433: CT sensor
335, 435: cephalometric sensor
336, 436: second sensor mounting part
234, 434: CT sensor mounting part

BEST MODE FOR CARRYING OUT THE INVENTION

Hereinafter, an explanation on an X-ray photographing apparatus according to the present invention will be given with reference to the attached drawings. However, the present invention will be described with reference to the particular illustrative embodiments, but it is not to be restricted by the embodiments. Wherever possible, the same reference numerals will be used through the drawings and the description to refer to the same or like parts.

Figure 1:
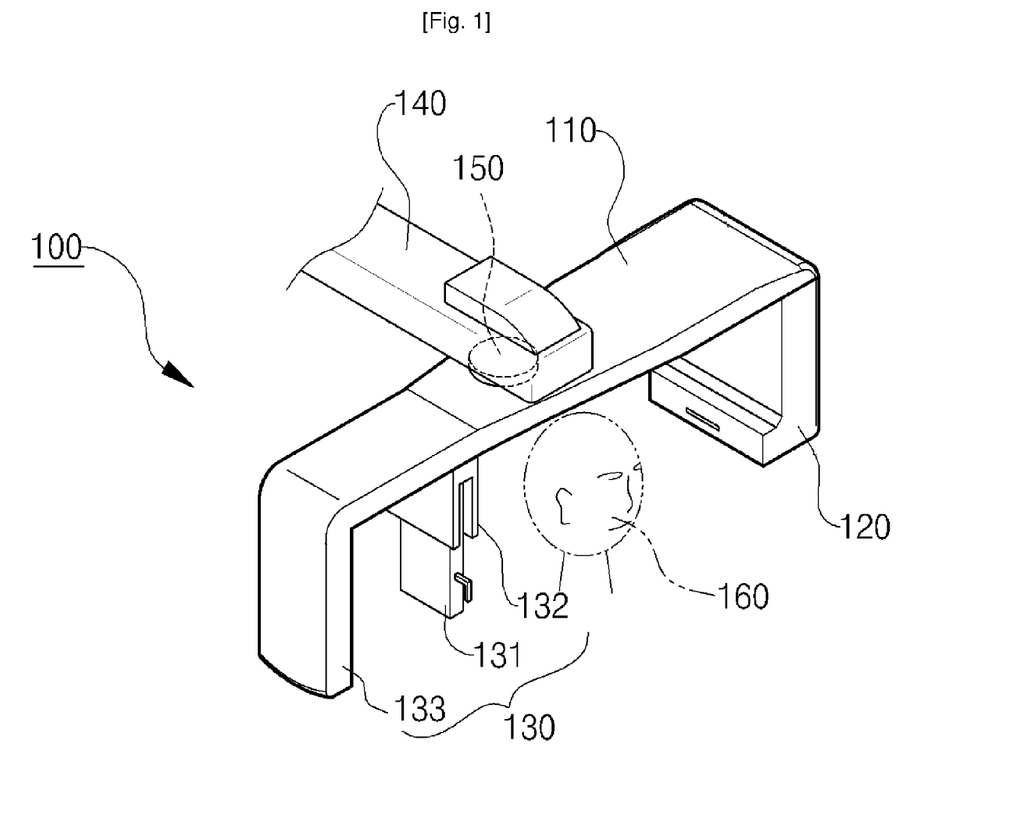
FIGS. 1 and 2 show an X-ray photographing apparatus according to a first embodiment of the present invention.
Figure 2:
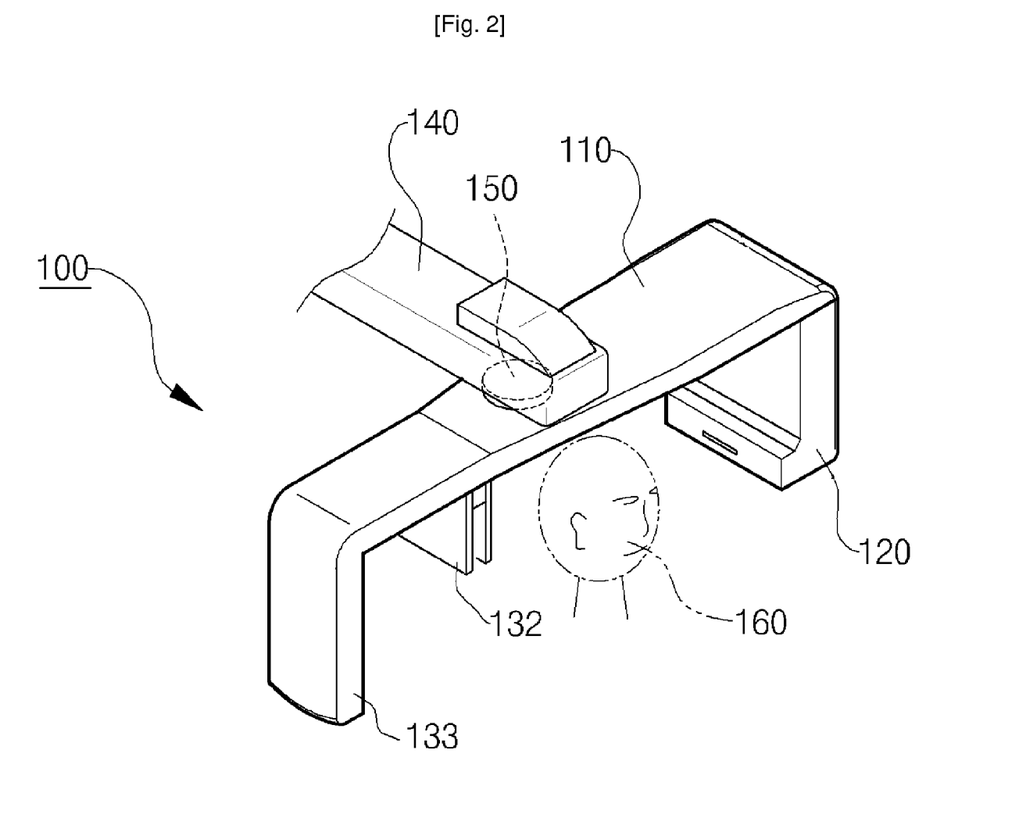

FIGS. 1 and 2 show an X-ray photographing apparatus according to a first embodiment of the present invention.

Referring to FIGS. 1 and 2, the X-ray photographing apparatus 100 according to the first embodiment of the present invention includes a rotary arm 110, an X-ray light source unit 120, an X-ray sensor unit 130, a rotary arm-supporting member 140, and a rotary arm-driving means 150, thereby performing panoramic and CT photographing.

The rotary arm 110 is connected to the X-ray light source unit 120 at one end thereof and to the X-ray sensor unit 130 at the other end thereof. The X-ray light source unit 120 and the X-ray sensor unit 130 are disposed to face each other. Further, the rotary arm 110 is supported by means of the rotary arm-supporting member 140 and driven by means of the rotary arm-driving means 150 to follow tracks to be made for performing the panoramic or CT photographing.

The X-ray light source unit 120 generates X-rays and irradiates them to a subject 160 to be photographed. The X-ray light source unit 120 has an X-ray source and a collimator mounted therein, such that the generated X-rays are passed through the subject 160 and irradiated to the X-ray sensor unit 130.

The X-ray sensor unit 130 receives the X-rays and converts them into electrical signals, that is, it detects the X-rays generated from the X-ray light source unit 120, obtains images from the detected X-rays, and sends the images to the outside.

The X-ray sensor unit 130 has a CT sensor 133 fixed thereon and a first sensor mounting part 132 adapted to detachably mount a panoramic sensor 131 thereonto. At this time, the first sensor mounting part 132 is disposed on the bottom surface of the rotary arm 110 in such a manner as to be closer to the X-ray light source unit 120 than the CT sensor 133 is.

At this time, the distance between the X-ray light source unit 120 and the panoramic sensor 131 and the distance between the X-ray light source unit 120 and the CT sensor 133 are adjusted previously in accordance with optimal magnification.

In case where the panoramic photographing is performed by using the X-ray photographing apparatus 100 according to the first embodiment of the present invention, as shown in FIG. 1, the panoramic sensor 131 is mounted onto the first sensor mounting part 132, thereby performing the panoramic photographing. That is, the X-ray photographing apparatus 100 is automatically transformed to a panoramic photographing apparatus, if the panoramic sensor 131 is mounted onto the first sensor mounting part 132. Therefore, a program for performing the panoramic photographing is automatically executed in the X-ray photographing apparatus 100, such that the mechanical components like the rotary arm 110 are automatically adjusted to correspond to the panoramic photographing apparatus.

Further, in case where the CT photographing is performed by using the X-ray photographing apparatus 100 according to the first embodiment of the present invention, as shown in FIG. 2, the panoramic sensor 131 is demounted from the first sensor mounting part 132, such that the X-ray photographing apparatus 100 is automatically transformed to a CT photographing apparatus. Therefore, a program for performing the CT photographing is automatically executed in the X-ray photographing apparatus 100, such that the mechanical components like the rotary arm 110 are automatically adjusted to correspond to the CT photographing apparatus.

There are various methods for automatically transforming the X-ray photographing apparatus 100 to the panoramic photographing apparatus or the CT photographing apparatus according to the mounting or demounting of the panoramic sensor 131. For example, the first sensor mounting part 132 has a sensor mounted at a predetermined position thereof, for sensing whether the panoramic sensor 131 is mounted or not, and if the sensed signal is sent to a central processing unit, the X-ray photographing apparatus is transformed to the photographing apparatus having a corresponding mode by means of a control unit having the signal received from the central processing unit.

MODE FOR THE INVENTION

Figure 3:
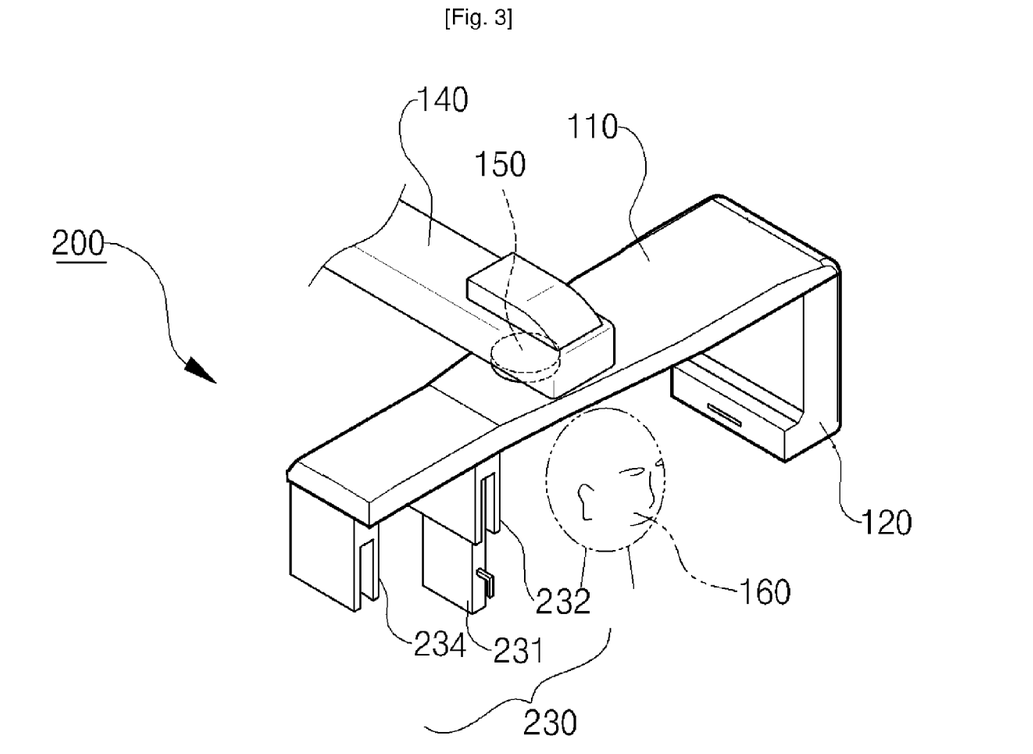
FIGS. 3 and 4 show an X-ray photographing apparatus according to a second embodiment of the present invention.
Figure 4:
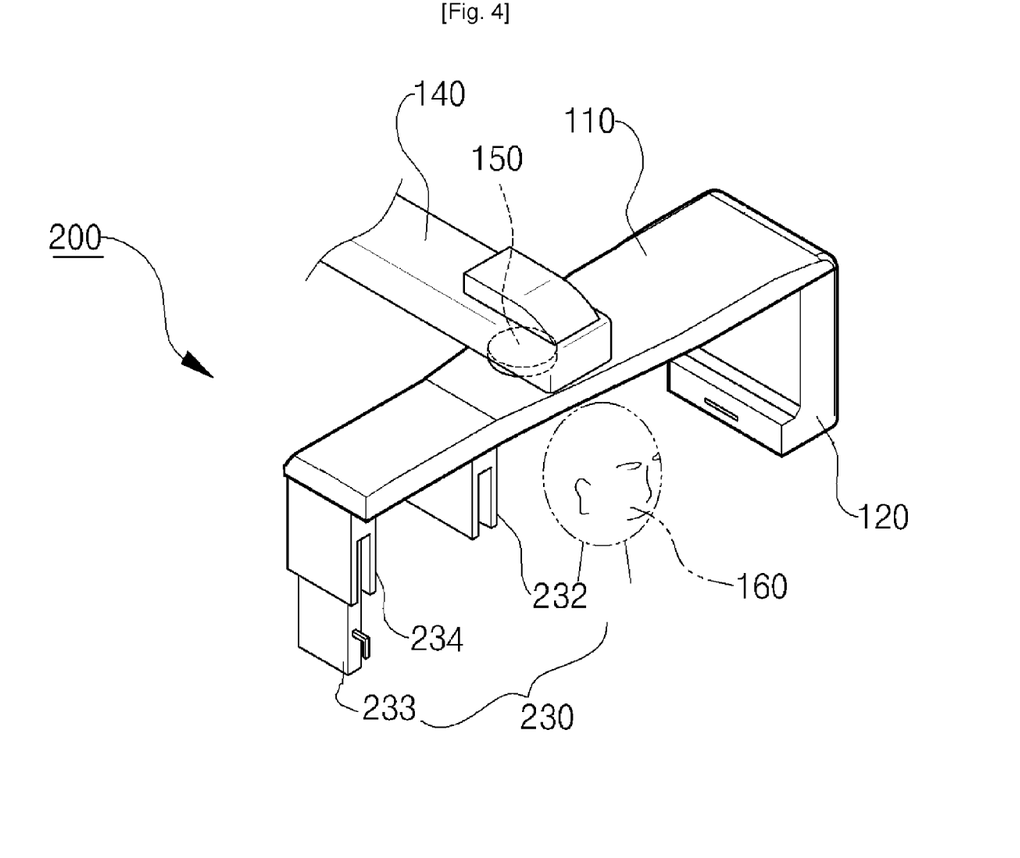

FIGS. 3 and 4 show an X-ray photographing apparatus according to a second embodiment of the present invention.

Referring to FIGS. 3 and 4, an X-ray photographing apparatus 200 according to the second embodiment of the present invention includes a rotary arm 110, an X-ray light source unit 120, an X-ray sensor unit 230, a rotary arm-supporting member 140, and a rotary arm-driving means 150, thereby performing panoramic and CT photographing.

The X-ray sensor unit 230 has a CT sensor mounting part 234 adapted to detachably mount a CT sensor 233 thereonto and a first sensor mounting part 232 adapted to detachably mount a panoramic sensor 231 thereonto.

At this time, the first sensor mounting part 232 is disposed on the bottom surface of the rotary arm 110 in such a manner as to be closer to the X-ray light source unit 120 than the CT sensor 233 is.

In case where the panoramic photographing is performed by using the X-ray photographing apparatus 200 according to the second embodiment of the present invention, the panoramic sensor 231 is mounted onto the first sensor mounting part 232, thereby performing the panoramic photographing. That is, the X-ray photographing apparatus 200 is automatically transformed to a panoramic photographing apparatus, if the panoramic sensor 231 is mounted onto the first sensor mounting part 232.

Further, in case where the CT photographing is performed by using the X-ray photographing apparatus 200 according to the second embodiment of the present invention, as shown in FIG. 4, the panoramic sensor 231 is demounted from the first sensor mounting part 232 and the CT sensor 233 is mounted onto the CT sensor mounting part 234, thereby performing the CT photographing, such that the X-ray photographing apparatus 200 is automatically transformed to the CT photographing apparatus.

The X-ray photographing apparatus 200 according to the second embodiment of the present invention are the same as that according to the first embodiment of the present invention, excepting the above-mentioned description.

Figure 5:
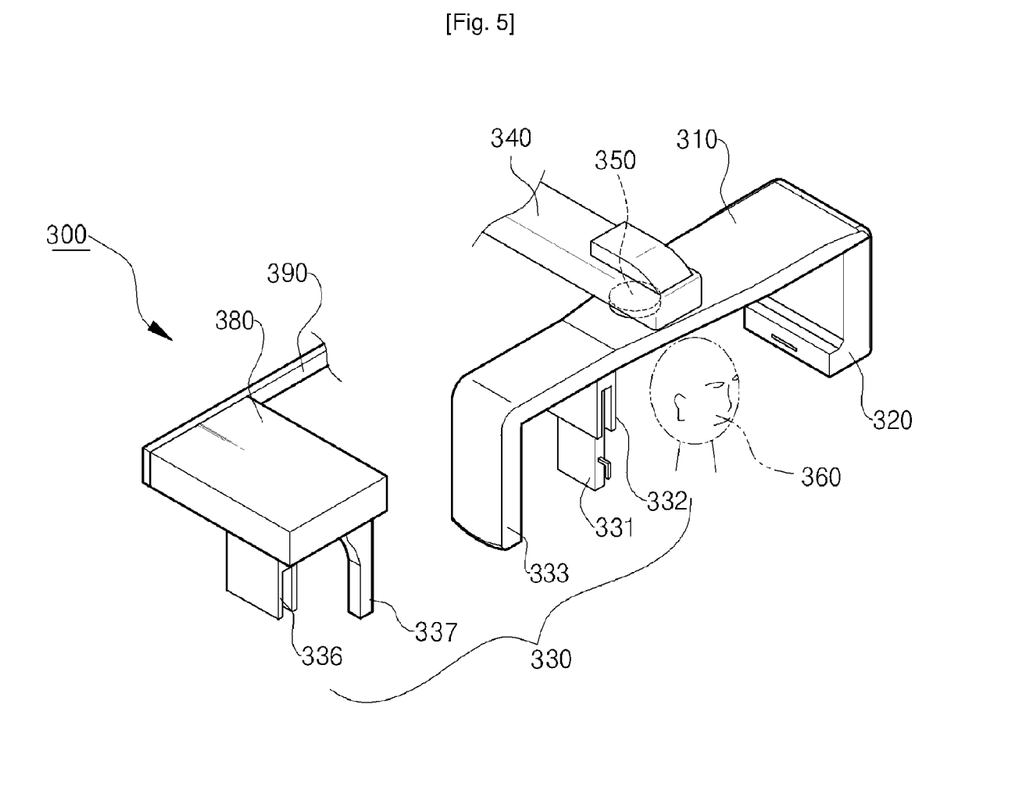
FIGS. 5-7 show an X-ray photographing apparatus according to a third embodiment of the present invention.
Figure 6:
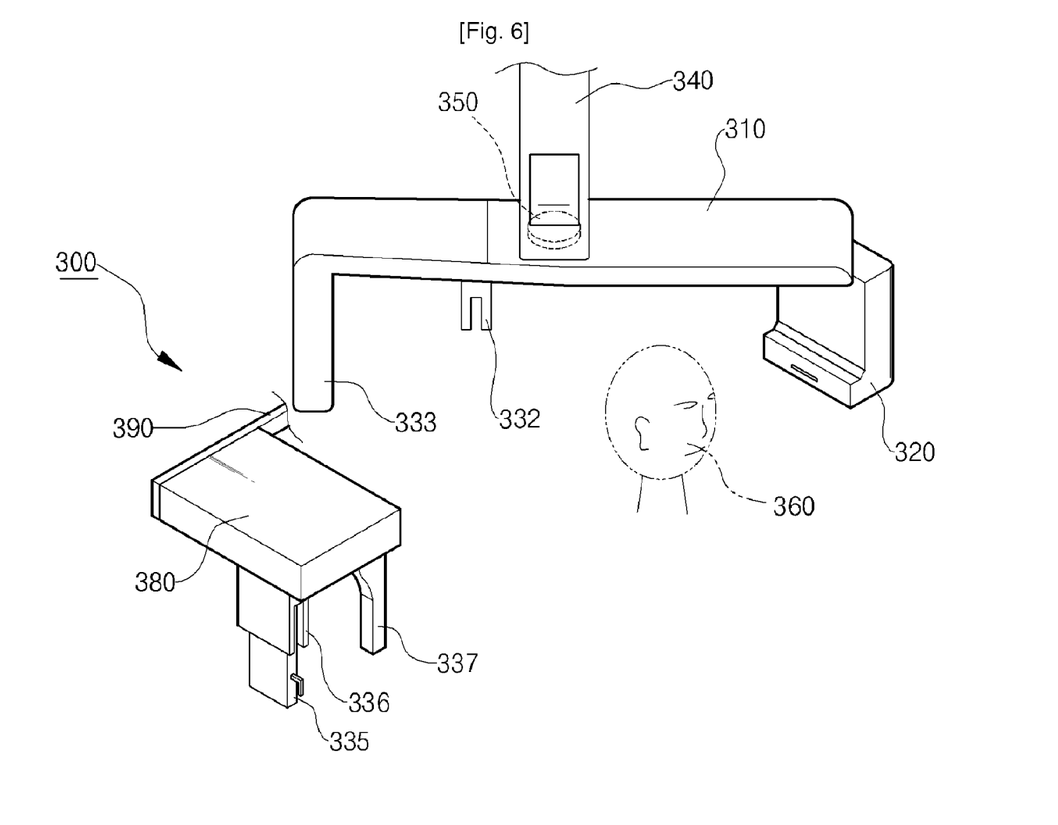
Figure 7:
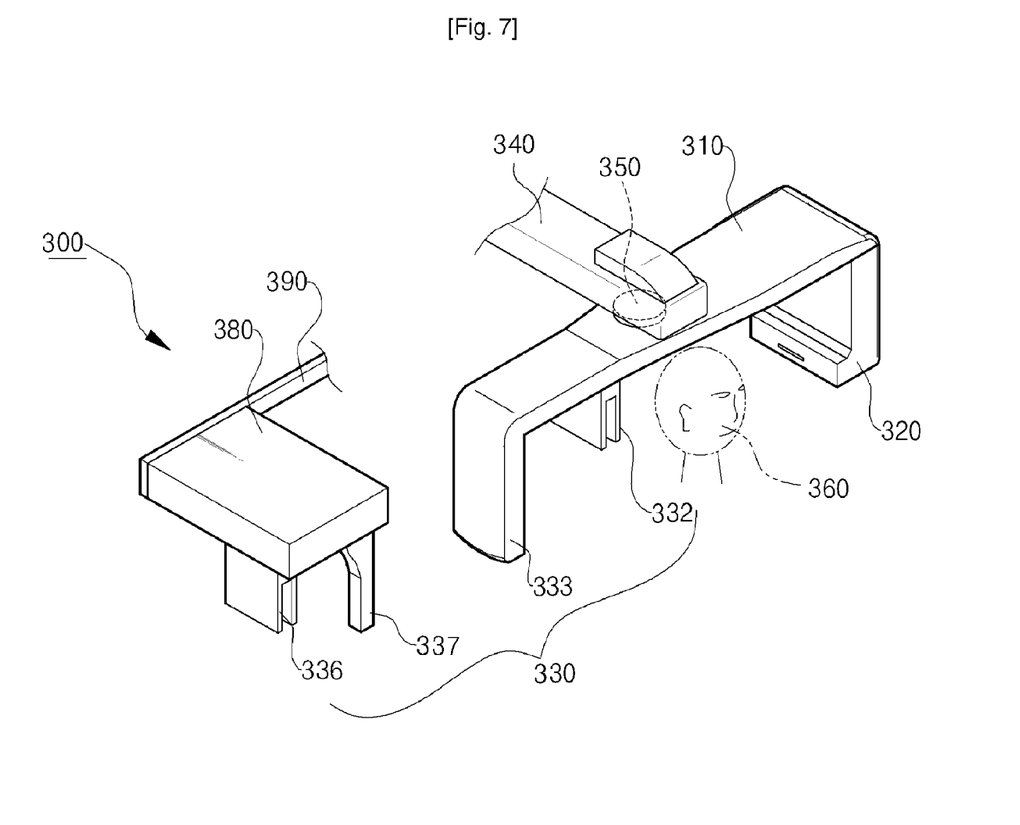

FIGS. 5-7 show an X-ray photographing apparatus according to a third embodiment of the present invention.

Referring to FIGS. 5-7, the X-ray photographing apparatus 300 according to the third embodiment of the present invention includes a rotary arm 310, a horizontal arm 380, an X-ray light source unit 320, an X-ray sensor unit 330, a rotary arm-supporting member 340, and a rotary arm-driving means 350, thereby performing panoramic, CT, and cephalometric photographing.

The rotary arm 310 is connected to the X-ray light source unit 320 at one end thereof and to the X-ray sensor unit 330 at the other end thereof. The X-ray sensor unit 330 has a first sensor mounting part 332 adapted to detachably mount a panoramic sensor 331 thereonto and a CT sensor 333. Further, the rotary arm 310 is supported by means of the rotary arm-supporting member 340 and driven by means of the rotary arm-driving means 350 to follow tracks to be made for performing the panoramic or CT photographing.

The X-ray light source unit 320 is driven separately from the rotary arm 310. That is, a driving means (not shown) for driving the X-ray light source unit 320 is located at a portion where the rotary arm 340 and the X-ray light source unit 320 are connected to each other, so that the X-ray light source unit 320 can be driven separately. Therefore, the X-ray light source unit 320 can be driven horizontally toward a direction adjacent to the X-ray sensor unit 330 or distant therefrom, separately from the rotary arm 340. In case of the cephalometric photographing, further, the X-ray light source unit 320 is horizontally driven by means of the driving means, separately from the rotary arm 340, or it is tilted to a predetermined direction.

The horizontal arm 380 has a second sensor mounting part 336 mounted at one end thereof, so as to detachably mount a cephalometric sensor 335 thereonto and a collimator 337 mounted at the other end thereof. Also, the horizontal arm 380 is supported by means of a connecting member 390.

In case where the panoramic photographing is performed by using the X-ray photographing apparatus 300 according to the third embodiment of the present invention, as shown in FIG. 5, the panoramic sensor 331 is mounted onto the first sensor mounting part 332, thereby performing the panoramic photographing. That is, the X-ray photographing apparatus 300 is automatically transformed to a panoramic photographing apparatus, if the panoramic sensor 331 is mounted onto the first sensor mounting part 332.

Further, in case where the cephalometric photographing is performed by using the X-ray photographing apparatus 300 according to the third embodiment of the present invention, as shown in FIG. 6, the panoramic sensor 331 is demounted from the first sensor mounting part 332, and the cephalometric sensor 335 is mounted onto the second sensor mounting part 336, thereby performing the cephalometric photographing. At this time, the cephalometric sensor 335 can be used as the panoramic sensor 331 used for the panoramic photographing. That is, if the panoramic sensor 331 is mounted onto the second sensor mounting part 336, the X-ray photographing apparatus 300 is automatically transformed to the cephalometric photographing apparatus. Therefore, the rotary arm 310 is automatically adjusted to be rotatably driven by the rotary arm-driving means 350 to a predetermined angle, and the X-ray light source unit 320 is automatically adjusted by means of the driving means for driving the X-ray light source unit 320 in such a manner as to be tilted to a predetermined angle and face the cephalometric sensor 335.

Furthermore, in case where the CT photographing is performed by using the X-ray photographing apparatus 300 according to the third embodiment of the present invention, as shown in FIG. 7, the panoramic sensor 331 and the cephalometric sensor 335 are respectively demounted from the first sensor mounting part 332 and the second sensor mounting part 336, thereby performing the CT photographing. That is, if the panoramic sensor 331 and the cephalometric sensor 335 are respectively demounted from the first sensor mounting part 332 and the second sensor mounting part 336, the X-ray photographing apparatus 300 is automatically transformed to the CT photographing apparatus.

The X-ray photographing apparatus 300 according to the third embodiment of the present invention are the same as that according to the first embodiment of the present invention, excepting the above-mentioned description.

Figure 8:
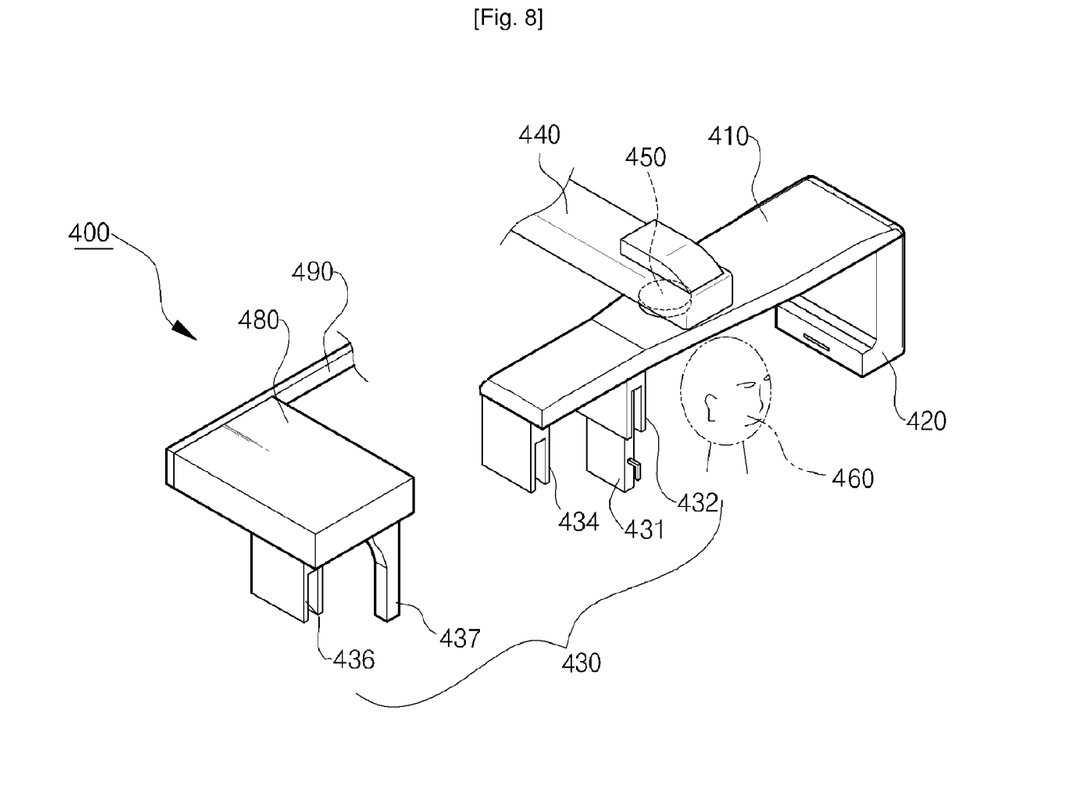
FIGS. 8-10 show an X-ray photographing apparatus according to a fourth embodiment of the present invention.
Figure 9:
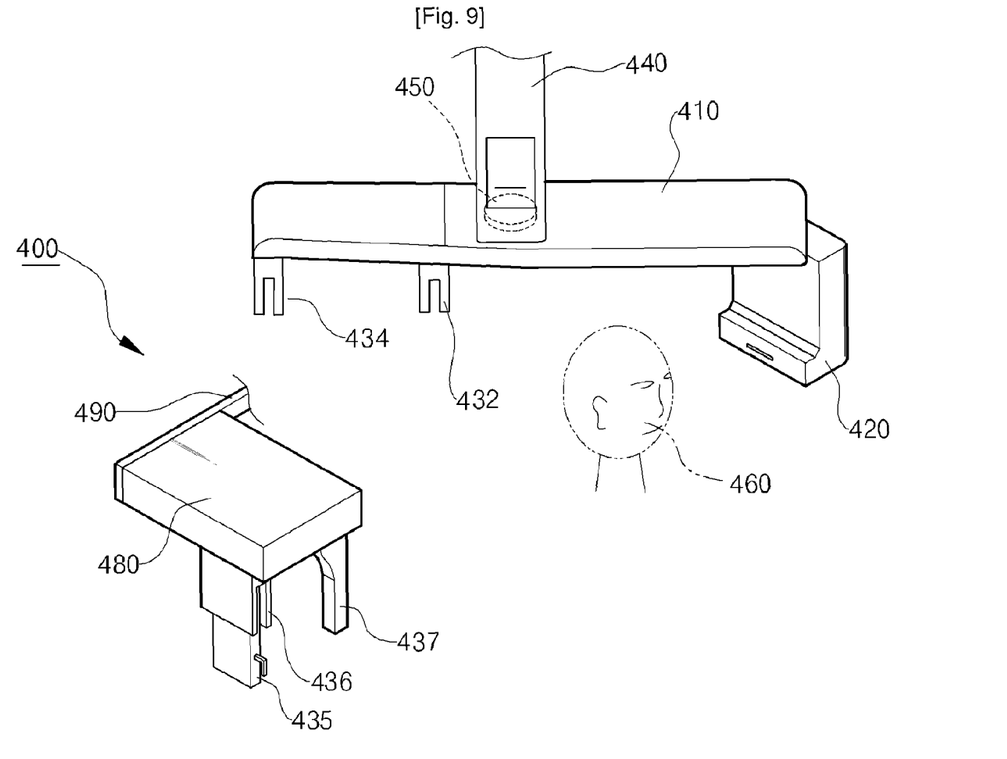
Figure 10:
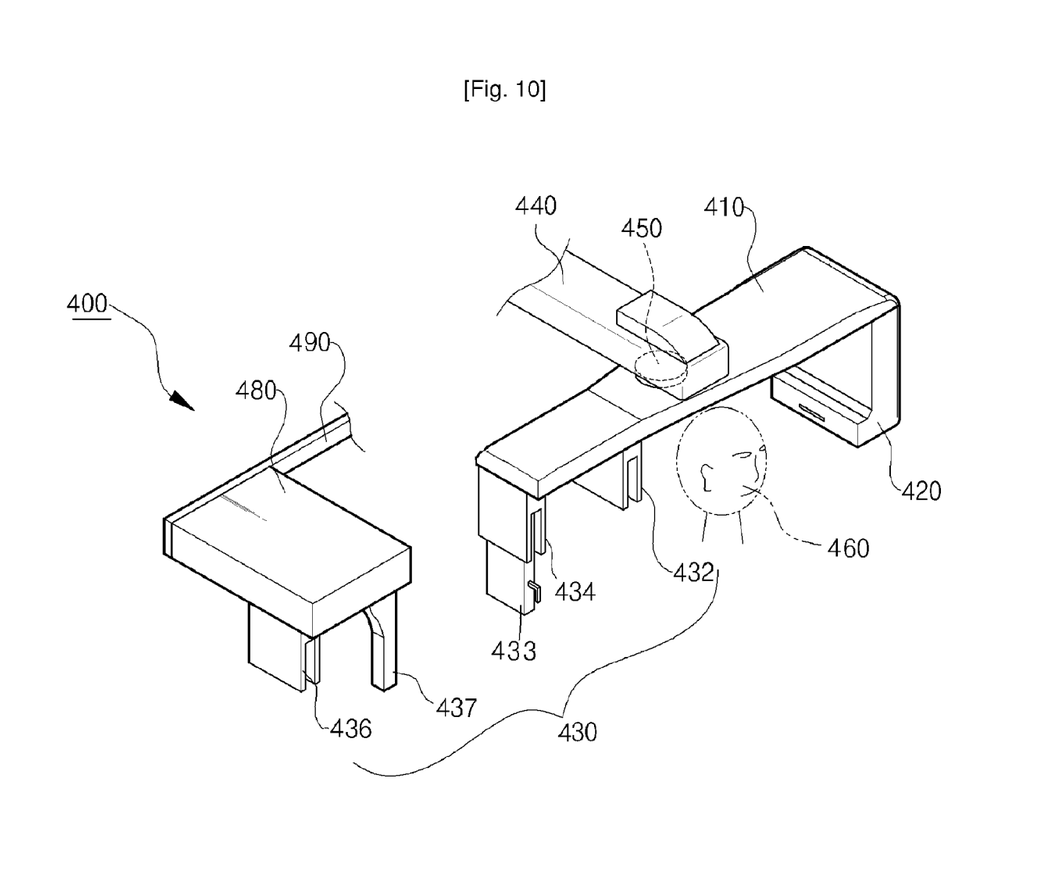

FIGS. 8-10 show an X-ray photographing apparatus according to a fourth embodiment of the present invention.

Referring to FIGS. 8-10, the X-ray photographing apparatus 400 according to the fourth embodiment of the present invention includes a rotary arm 410, a horizontal arm 480, an X-ray light source unit 420, an X-ray sensor unit 430, a rotary arm-supporting member 440, and a rotary arm-driving means 450, thereby performing panoramic, CT, and cephalometric photographing.

The rotary arm 410 is connected to the X-ray light source unit 420 at one end thereof and to the X-ray sensor unit 430 at the other end thereof. The X-ray sensor unit 430 has a first sensor mounting part 432 adapted to detachably mount a panoramic sensor 431 thereonto and a CT sensor mounting part 434 adapted to detachably mount a CT sensor 333 thereonto.

The X-ray light source unit 420 is driven in a horizontal direction, separately from the rotary arm 410, or tilted to a predetermined angle.

The horizontal arm 480 has a second sensor mounting part 436 mounted at one end thereof, so as to detachably mount a cephalometric sensor 435 thereonto and a collimator 437 mounted at the other end thereof.

In case where the panoramic photographing is performed by using the X-ray photographing apparatus 400 according to the fourth embodiment of the present invention, as shown in FIG. 8, the panoramic sensor 431 is mounted onto the first sensor mounting part 432, thereby performing the panoramic photographing. That is, the X-ray photographing apparatus 400 is automatically transformed to a panoramic photographing apparatus, if the panoramic sensor 431 is mounted onto the first sensor mounting part 332.

Further, in case where the cephalometric photographing is performed by using the X-ray photographing apparatus 400 according to the fourth embodiment of the present invention, as shown in FIG. 9, the panoramic sensor 431 is demounted from the first sensor mounting part 432, and the cephalometric sensor 435 is mounted onto the second sensor mounting part 436, thereby performing the cephalometric photographing. At this time, the cephalometric sensor 435 can be used as the panoramic sensor 431 used for the panoramic photographing. That is, if the panoramic sensor 431 is mounted onto the second sensor mounting part 436, the X-ray photographing apparatus 400 is automatically transformed to the cephalometric photographing apparatus. Therefore, the rotary arm 410 is automatically adjusted to be rotatably driven by the rotary arm-driving means 450 to a predetermined angle, and the X-ray light source unit 420 is automatically adjusted in such a manner as to be tilted to a predetermined angle and face the cephalometric sensor 435. At this time, the CT sensor 433 is at a state of being separated from the CT sensor mounting part 434. Therefore, if the X-ray light source unit 420 and the cephalometric sensor 435 face each other, the X-ray light source unit 420 is tilted to the predetermined angle, without having any arrangement, thereby performing the cephalometric photographing.

Furthermore, in case where the CT photographing is performed by using the X-ray photographing apparatus 400 according to the fourth embodiment of the present invention, as shown in FIG. 10, the panoramic sensor 431 and the cephalometric sensor 435 are respectively demounted from the first sensor mounting part 432 and the second sensor mounting part 436, and the CT sensor 433 is mounted onto the CT sensor mounting part 434, thereby performing the CT photographing. That is, if the panoramic sensor 431 and the cephalometric sensor 435 are respectively demounted from the first sensor mounting part 432 and the second sensor mounting part 436 and the CT sensor 433 is mounted onto the CT sensor mounting part 434, the X-ray photographing apparatus 400 is automatically transformed to the CT photographing apparatus.

The X-ray photographing apparatus 400 according to the fourth embodiment of the present invention are the same as that according to the third embodiment of the present invention, excepting the above-mentioned description.

INDUSTRIAL APPLICABILITY

According to the present invention, there is provided an X-ray photographing apparatus that is capable of being automatically transformed to panoramic, CT, or cephalometric photographing apparatuses having a corresponding mode in accordance with the mounting or demounting of a panoramic sensor, a CT sensor, or a cephalometric sensor thereon/therefrom, thereby at once performing the photographing for the images in a plurality of modes.

The invention claimed is:

1. An X-ray photographing apparatus having an X-ray light source unit for generating X-rays therefrom and an X-ray sensor unit for detecting the X-rays generated from the X-ray light source unit, wherein the X-ray sensor unit has a first sensor mounting part adapted to detachably mount a panoramic sensor thereonto and a CT sensor mounting part adapted to detachably mount a CT sensor thereonto, such that if the panoramic sensor is mounted onto the first sensor mounting part, the X-ray photographing apparatus is transformed to a panoramic X-ray photographing apparatus, and if the panoramic sensor is demounted from the first sensor mounting part and the CT sensor is mounted onto the CT sensor mounting part, the X-ray photographing apparatus is transformed to a CT X-ray photographing apparatus.

2. The X-ray photographing apparatus according to claim 1, wherein the first sensor mounting part is located closer to the X-ray light source unit than the CT sensor is.

3. An X-ray photographing apparatus having an X-ray light source unit for generating X-rays therefrom and an X-ray sensor unit for detecting the X-rays generated from the X-ray light source unit, wherein the X-ray sensor unit has a CT sensor mounting part adapted to detachably mount a CT sensor thereonto and a first sensor mounting part and a second sensor mounting part each adapted to detachably mount an X-ray sensor used for panoramic photographing or cephalometric photographing thereonto, such that if the X-ray sensor is mounted onto the first sensor mounting part, the X-ray photographing apparatus is transformed to a panoramic X-ray photographing apparatus; if the X-ray sensor is mounted onto the second sensor mounting part, the X-ray photographing apparatus is transformed to a cephalometric X-ray photographing apparatus;

and if the X-ray sensor is demounted from the first sensor mounting part and the second sensor mounting part and the CT sensor is mounted onto the CT sensor mounting part, the X-ray photographing apparatus is transformed to a CT X-ray photographing apparatus.

4. The X-ray photographing apparatus according to claim 3, wherein the first sensor mounting part is located closer to the X-ray light source unit than the CT sensor is.

* * * * *